(12) United States Patent
Fahmy et al.

(10) Patent No.: US 11,098,300 B2
(45) Date of Patent: Aug. 24, 2021

(54) METHOD FOR THE PREPARATION OF NANOSCALE DNA-ENCIRCLED LIPID BILAYERS

(71) Applicants: TECHNISCHE UNIVERSITÄT DRESDEN, Dresden (DE); HELMHOLTZ-ZENTRUM DRESDEN—ROSSENDORF E.V., Dresden (DE)

(72) Inventors: Karim Fahmy, Dresden (DE); Thorsten-Lars Schmidt, Dresden (DE); Katarina Iric, Dresden (DE)

(73) Assignees: TECHNISCHE UNIVERSITÄT DRESDEN, Dresden (DE); HELMHOLTZ-ZENTRUM DRESDEN—ROSSENDORF E.V., Dresden (DE)

(*) Notice: Subject to any disclaimer, the term of this patent is extended or adjusted under 35 U.S.C. 154(b) by 0 days.

(21) Appl. No.: 16/959,841

(22) PCT Filed: Feb. 21, 2019

(86) PCT No.: PCT/EP2019/054271
§ 371 (c)(1),
(2) Date: Jul. 2, 2020

(87) PCT Pub. No.: WO2019/162357
PCT Pub. Date: Aug. 29, 2019

(65) Prior Publication Data
US 2020/0407707 A1    Dec. 31, 2020

(30) Foreign Application Priority Data
Feb. 21, 2018   (EP) .................................. 18157852

(51) Int. Cl.
*C12N 15/09*     (2006.01)
*C12N 15/10*     (2006.01)
(Continued)

(52) U.S. Cl.
CPC ......... *C12N 15/101* (2013.01); *G01N 21/553* (2013.01); *G01N 29/022* (2013.01);
(Continued)

(58) Field of Classification Search
CPC ...... C12N 15/10; C12N 15/101; C12N 15/09; C12Q 1/68; G01N 33/68; G01N 21/553;
(Continued)

(56) References Cited

U.S. PATENT DOCUMENTS

2017/0232114 A1*   8/2017   Lehr ..................... A61K 9/1271
                                                                                     424/450
2018/0237800 A1*   8/2018   Murthy .................. C12N 11/08
(Continued)

FOREIGN PATENT DOCUMENTS

WO     2017/118862 A1     7/2017

OTHER PUBLICATIONS

International Search Report and Written Opinion of the International Searching Authority for International Application No. PCT/EP2019/054271 dated Mar. 14, 2019.
(Continued)

*Primary Examiner* — Brian J. Sines
(74) *Attorney, Agent, or Firm* — Heslin Rothenberg Farley & Mesiti P.C.

(57) ABSTRACT

The present invention relates to a method for the preparation of nanoscale nucleic acid-encircled lipid bilayers, the nanoscale nucleic acid-encircled lipid bilayers and their use.

20 Claims, 7 Drawing Sheets

Figure 1A:
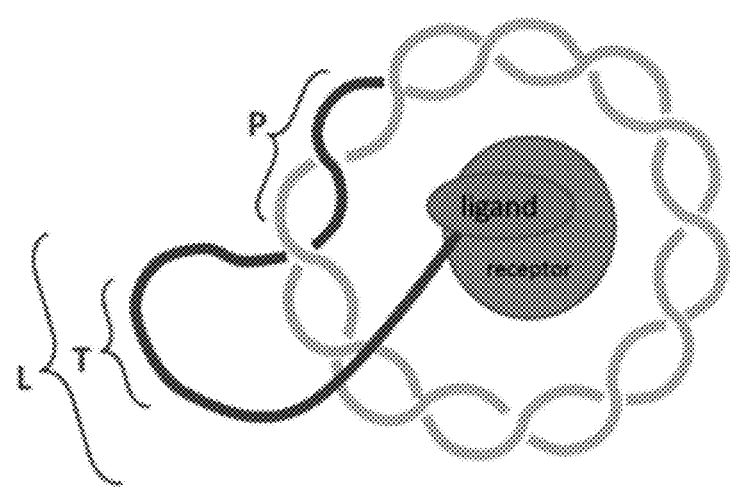

(51) Int. Cl.
*G01N 21/552* (2014.01)
*G01N 29/02* (2006.01)
*G01N 30/02* (2006.01)
*G01N 30/38* (2006.01)

(52) U.S. Cl.
CPC ....... *G01N 30/02* (2013.01); *G01N 2030/027* (2013.01); *G01N 2030/385* (2013.01)

(58) Field of Classification Search
CPC ...... G01N 29/022; B82Y 40/00; B82Y 15/00; B82B 1/00; B82B 3/00
See application file for complete search history.

(56) References Cited

U.S. PATENT DOCUMENTS

| | | | | |
|---|---|---|---|---|
| 2019/0262469 | A1* | 8/2019 | Brinker | A61K 47/6923 |
| 2019/0323002 | A1* | 10/2019 | Gopinath | G01N 33/573 |
| 2020/0025757 | A1* | 1/2020 | Gopinath | G01N 21/47 |
| 2020/0407707 | A1* | 12/2020 | Fahmy | B82Y 40/00 |

OTHER PUBLICATIONS

Iric, K., et al., "DNA-encircled lipid bilayers", Nanoscale, vol. 10, pp. 18463-18467 (2018).

Czogalla, A., et al., "DNA Nanostructures on Membranes as Tools for Synthetic Biology", Biophysical Journal, vol. 110, pp. 1698-1707 (2016).

Xu, W., et al., "A Programmable DNA Origami Platform to Organize SNAREs for Membrane Fusion", Journal of the American Chemical Society, vol. 138, No. 13, pp. 4439-4447 (2016).

Xu, W., et al., "Supporting Information; A Programmable DNA Origami Platform to Organize SNAREs for Membrane Fusion", Journal of the American Chemical Society, vol. 138, No. 13, pp. S1-S28 (2016).

Schmidt, T.L., et al., "Potyamide Struts for DNA Architectures", Angew. Chem. Int. Ed., vol. 46, pp. 4382-4384 (2007).

Schmidt, T.L., et al., "Construction of a Structurally Defined Double-Stranded DNA Catenane", Nano Letters, vol. 11, pp. 1739-1742 (2011).

Schmidt, T.L., et al., "Supporting Information for: Construction of a Structurally Defined Double Stranded DNA Catanane", Nano Letters, vol. 11, pp. 1-5 (2011).

Langecker, M., et al., "DNA Nanostructures Interacting with Lipid Bilayer Membranes", Acc. Chem. Res., vol. 47, pp. 1807-1815 (2014).

Perrault, S.D., et al., "Virus-Inspired Membrane Encapsulation of DNA Nanostructures to Active In Vivo Stability", ACS Nano, vol. 8, No. 5, pp. 5132-5140 (2014).

Zhang, Z., et al., "Placing and shaping liposomes with reconfigurable DNA nanocages", Nature Chemistry, vol. 9, pp. 653-659 (2017).

Chan, Y., et al., "Effects of linker sequences on vesicle fusion mediated by lipid-anchored DNA oligonucleotides", Proceedings of the National Academy of Sciences, vol. 106, No. 4, pp. 979-984 (2009).

Chang, T., et al., "Durable expression of minicircle DNA-Liposome-Delivered Androgen Receptor cDNA in Mice with Hepatocellular Carcinoma", BioMed Research International, vol. 2014, pp. 1-9 (2014).

Chan, Y., et al., "Lipid-anchored DNA mediates vesicle fusion as observed by lipid and content mixing", Biointerphases, vol. 3, No. 2, pp. FA17-FA21 (2008).

Loew, M., et al., "Lipid Domain Specific Recruitment of Lipophilic Nucleic Acids: A Key for Switchable Functionalization of Membranes", Journal of the American Chemical Society, vol. 132, pp. 16066-16072 (2010).

Langecker, M., et al., "Supplementary Materials for Synthetic Lipid Membrane Channels Formed by Designed DNA Nanostructures", Science, vol. 338, No. 6109, pp. 932-936 (2012).

Raschle, T., et al., "Controlled Co-reconstitution of Multiple Membrane Proteins in Lipid Bilayer Nanodiscs Using DNA as a Scaffold", ACS Chemical Biology, vol. 10, pp. 2448-2454 (2015).

Seeman, N.C., et al., "DNA nanotechnology", Nature Reviews, vol. 3, pp. 1-23 (2017).

* cited by examiner

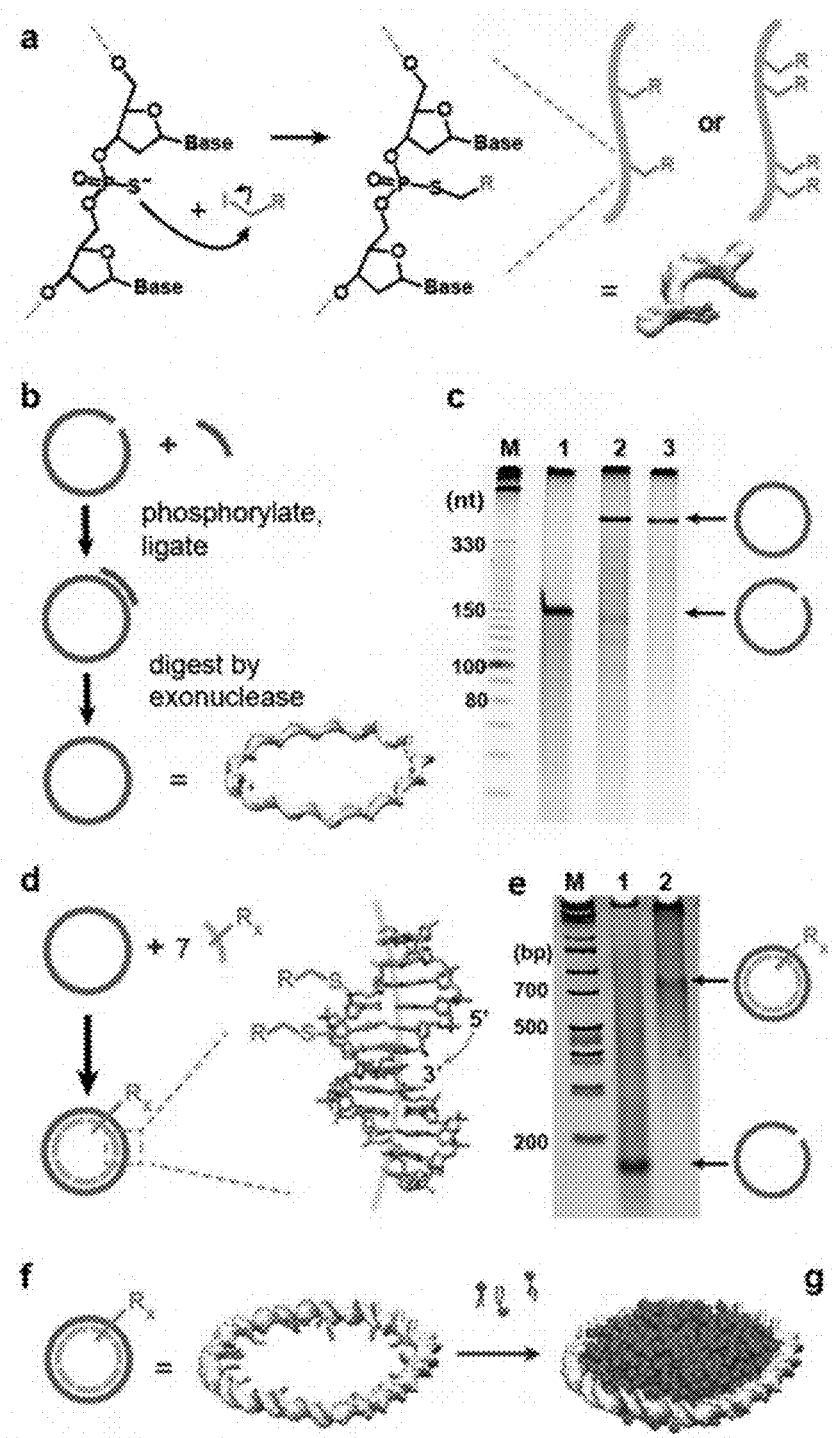
Fig. 3a-g

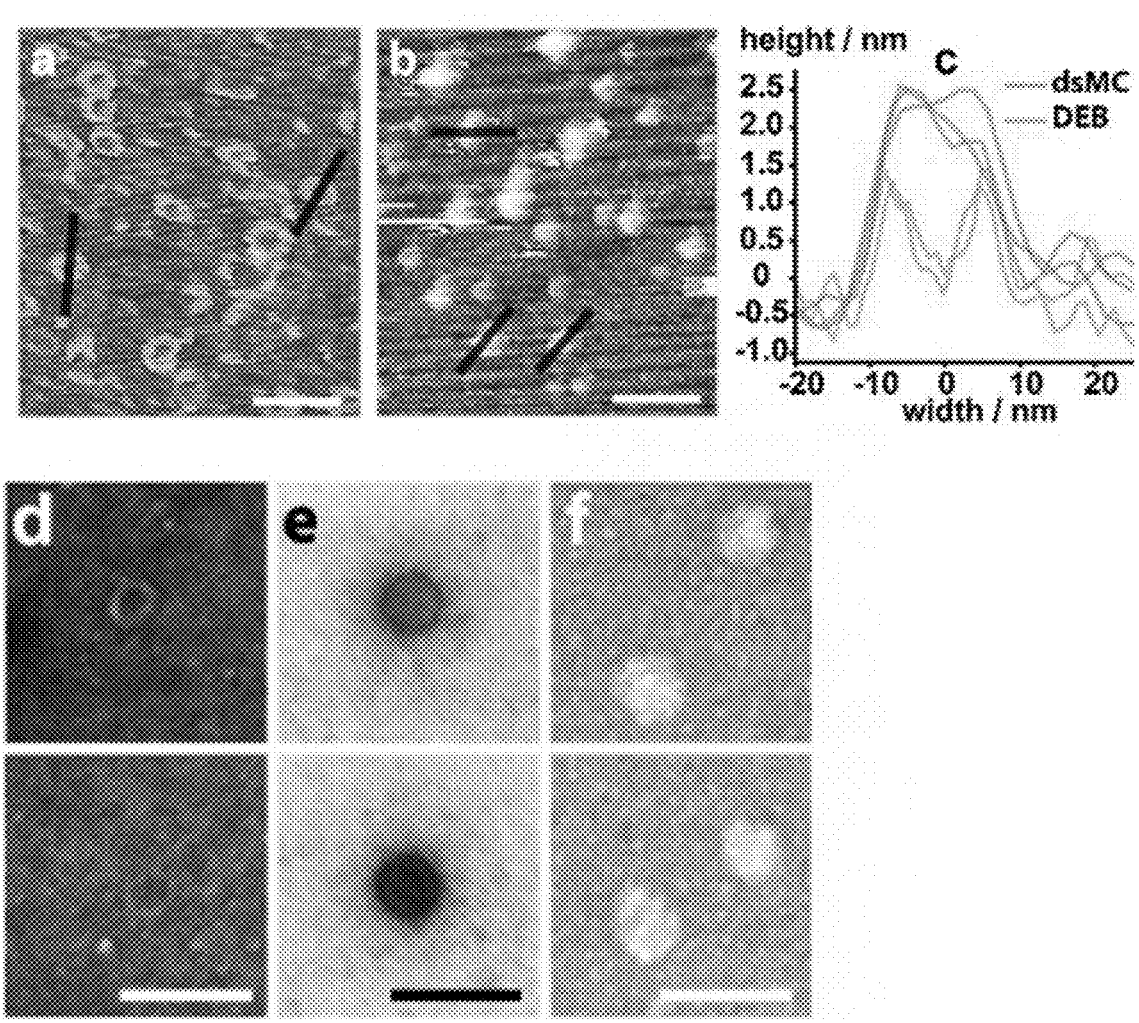
Fig. 4a-f

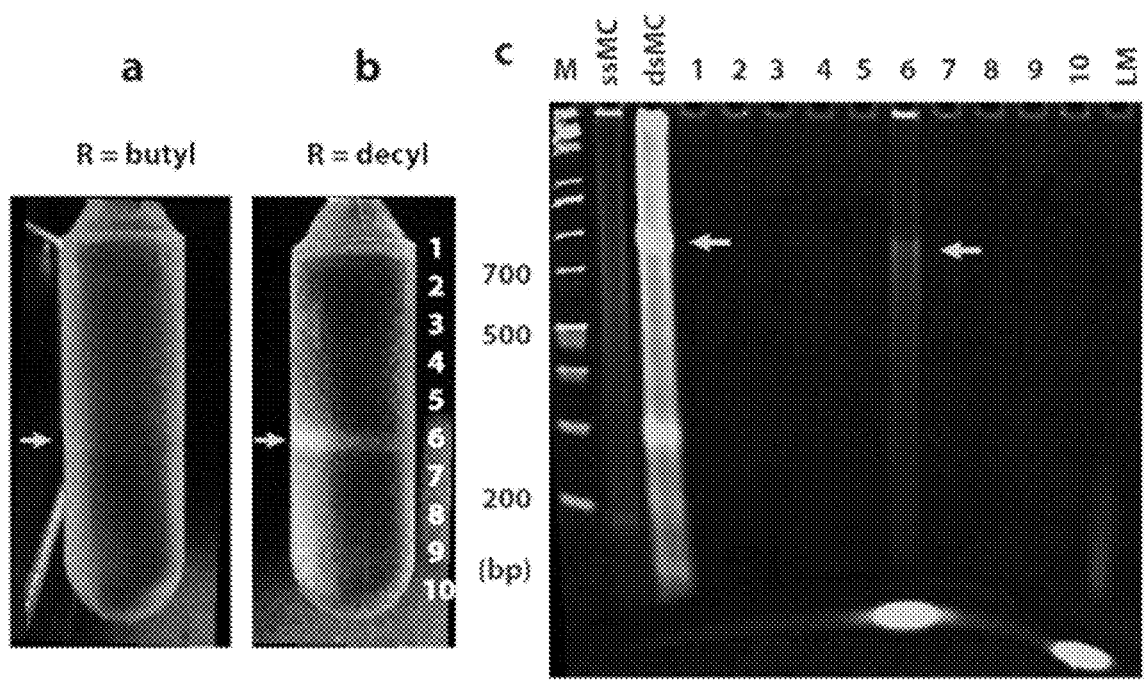
Fig. 5a-c
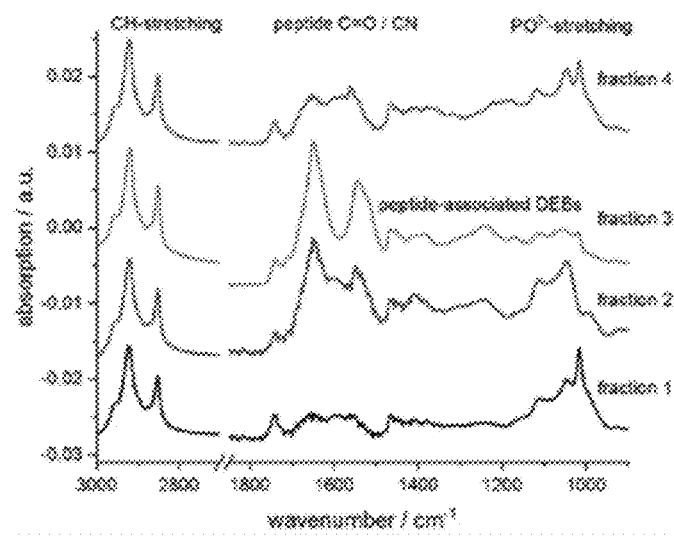
Fig. 6

METHOD FOR THE PREPARATION OF NANOSCALE DNA-ENCIRCLED LIPID BILAYERS

CROSS REFERENCE TO RELATED APPLICATIONS

This application is a national stage filing under section 371 of International Application No. PCT/EP2019/054271 filed on Feb. 21, 2019, and published on Aug. 29, 2019 as WO 2019/162357, which claims priority to European Application No. 18157852.7, filed on Feb. 21, 2018. The entire contents of WO 2019/162357 are hereby incorporated herein by reference.

The present invention relates to a method for the preparation of nanoscale DNA-encircled lipid bilayers, the nanoscale DNA-encircled lipid bilayers and their use.

A large number of scientific and pharmacological analysis techniques concern the properties of membrane proteins which are prime targets for currently used approved drugs. Membrane protein-targeting drugs account for the majority of sales on the pharmacological market. The in vitro analysis of membrane proteins requires their reconstitution into lipid bilayers as the natural microenvironment that supports their native structure and function. The state of the art offers two prominent methods.

The purification of membrane proteins from cell membranes by detergent solubilization and the ensuing incorporation into lipid bilayers. The latter can be provided by conventional spherical lipid vesicles (liposomes) of variable sizes typical in the 100 nm to 1 µm range.

Alternatively, membrane-scaffolding protein (MSP)-based reconstitution into lipid nanodiscs (NDs) of 10 to 20 nm diameter can be performed. In both cases, the membrane protein inserts in a self-assembly process upon removal of the respective detergent. The specific reconstitution conditions are typically specifically adapted to the membrane protein of interest.

The direct transfer of membrane proteins from cell membranes into discoidal lipid bilayers is possible with detergent-like polymers such as styrene maleic acid and its derivatives.

Both methods lead to lipid bilayers on the 10 to 20 nm scale which contain a single or a small number of membrane proteins per discoidal assembly which, in contrast to the vesicle system, do not exhibit an inside or outside distinction with respect to their orientation within the bilayer. Thereby, the membrane proteins are accessible from both their original extracellular and intracellular sides.

The method described above provides little control over membrane protein specificity, lipid and membrane protein stoichiometry per bilayer, leading to heterogeneous assemblies and of polydisperse bilayer discs containing potentially a mixture of all membrane proteins of a cell membrane. In contrast the prior art methods offer more control by adjusting the mixing ratio of a purified membrane protein with lipids and MSPs. The latter method has been improved recently by circularizing the MSPs such that the size variability in the final NDs, which originates from the open ring-shape of an individual MSP, could be reduced. Both procedures, however, suffer from the very restricted control of final disc diameters and the shape of MSP-derived NDs is not known but differs from a symmetric circular disc. Furthermore, for a given MSP the size of the NDs still varies in relation to the amount of lipids used for the reconstitution. Both, NDs and polymer encircled bilayers do not enable the free design of super-assemblies of individual discs into higher multimeric structures, because of the lack of stoichiometrically defined chemical interaction sites and the restricted possibility of introducing such sites into polymers and MSPs, respectively. In the latter case, mutagenesis is required to allow incorporating chemical functionalities, which thus interfere with protein stability.

Therefore, both methods are not suited to produce nanoscaled lipid bilayers with programmable chemical specificities for their assembly or immobilization on surfaces. Both possibilities would provide enormous advantages for membrane protein structure determinations by x-ray diffraction or for the high-throughput screening of drugs against surface immobilized membrane proteins.

To this end, methods from structural DNA nanotechnology shall be used. DNA can be used as a material to build up almost arbitrary shapes and structures (1). Particularly, the robust DNA origami method, for which a template strand of around 7500 nucleotides is folded with hundreds of synthetic oligonucleotides is used, is frequently used due to its robustness to build large, megadalton-sized structures typically measuring tens to hundreds of nanometers. However, for much smaller assemblies, such as DNA minicircles (2, 3), different construction principles involving few synthetic oligonucleotides can be better suited and are more economical. DNA structures can be functionalized with a large variety of artificial elements in a modular and programmable fashion. To enable interactions between negatively charged hydrophilic DNA and lipids, several oligonucleotide modifications have been previously employed including cholesterol, porphyrin or phospholipid modifications (4-6).

It is therefore an object of the present invention to overcome the drawbacks of the prior art.

In a first aspect the invention provides a minicircle-surrounded lipid bilayer. The minicircle comprises at least nucleic acids or nucleic acid analogues, wherein the bilayer comprises at least one membrane associated entity.

In a further aspect the present invention provides a method for the preparation of minicrcle-surrounded lipid bilayers. The method comprises the steps of:
a) providing a minicircle comprising at least double stranded nucleic acids or nucleic acid analogues,
b) mixing of the minicircle with lipids and the membrane associated entity in a detergent,
c) remove of the detergent,
d) self-assembly of the minicircle-surrounded lipid bilayer comprising the membrane associated entity In a further aspect the present invention provides a method for preparation of DNA-surrounded lipid bilayers. The method comprises the steps of:
a) providing a circular ssDNA strand,
b) providing a complementary ssDNA sequence or partial complementary ssDNA sequences,
c) assembly of the dsDNA,
d) mixing of the dsDNA with lipids and the membrane associated entity in a detergent,
e) remove of the detergent,
f) self-assembly of the DNA-surrounded lipid bilayer comprising the membrane associated entity.

In a further aspect the invention provides an assay comprising the minicircle-surrounded lipid bilayer.

In a further aspect the invention provides an assay comprising the DNA-surrounded lipid bilayer.

In a further aspect the invention provides a method for determining the interaction of a membrane associated entity and a target molecule. The method comprises the steps:
a) Providing an assay according to invention, b) Providing a target molecule,
c) Determining the interaction of the at least one membrane associated entity and the target molecule.

For the purpose of realizing the invention, it is also beneficial to combine the variants and embodiments according the invention described previously and the features of the claims in any order.

Figure 1B:
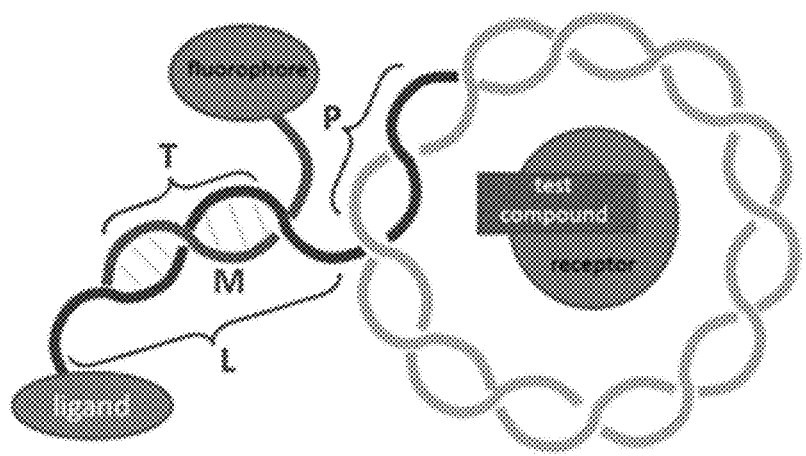
Figure 2:
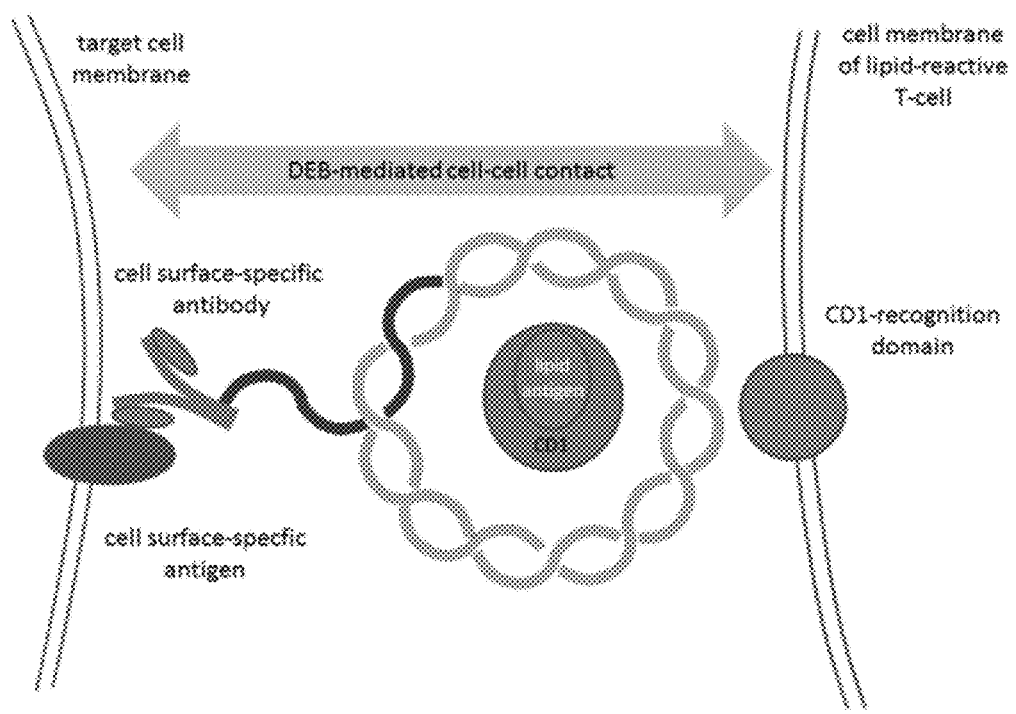
Figure 7:
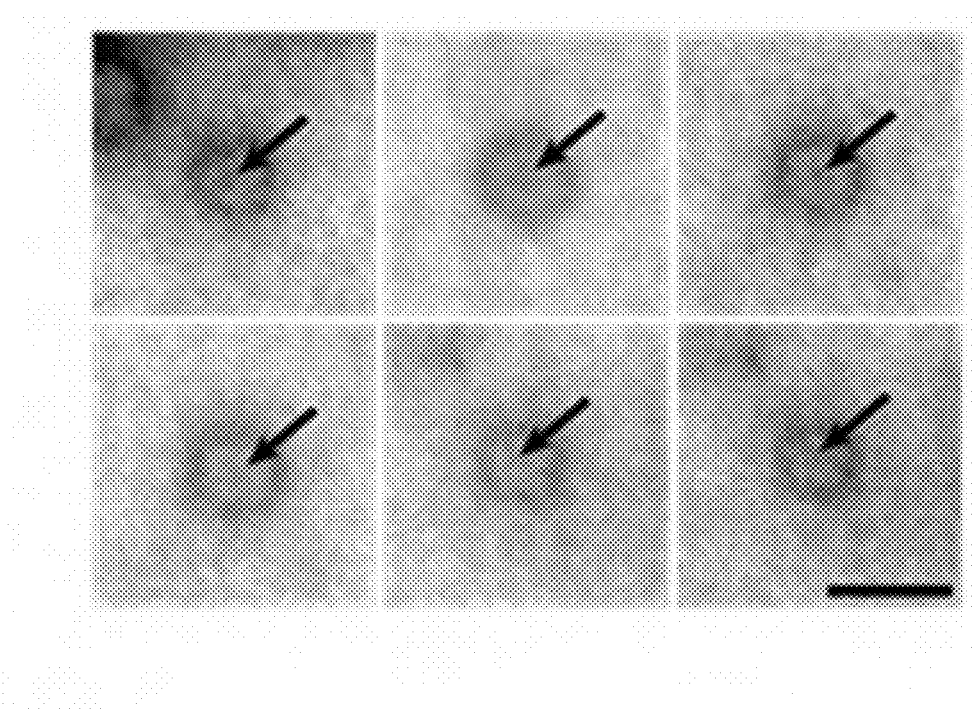

FIG. 1a schematically depicts a DNA-encircled lipid bilayer (DEB) with ligand, covalently linked to an oligonucleotide that is hybridized to the dsDNA minicircle, in FIG. 1b, c shows a ligand and a receptor-targeting compound, which are tethered to a DEB, in FIG. 2 shows the use of the DEBs for targeting cells for T-cell interactions and in FIG. 3 shows schematically the synthesis of the DNA minicircle surrounding the lipid bilayer, FIG. 4 shows size and shape analysis of dsMCs and DEBs: Atomic Force Microscopy (AFM) image of a) empty dsMCs (147 base pairs with 4 butyl groups per hybridized 21-mer) and (b) corresponding DEBs filled with di-myristoyl-phosphatidylcholine and 10% dimyristoyl-3-trimethylammonium-propane, c) height profiles, d) Transmission Scanning Electron Microscopy (tSEM) images of empty dsMCs, e) tSEM image of a DEB with 14 ethyl modifications (positively stained), f) tSEM image of a DEB with 28 decyl modifications, FIG. 5 shows analysis of DEBs: Iodixanol gradient ultracentrifugation of Rhodamine-PE-containing DEBs with (a) 28 butyl groups, and (b) 28 decyl groups, that were analyzed by (c) native SDS PAGE (LM=control lipid mix), FIG. 6 shows vibrational spectra obtained from consecutively collected size exclusion chromatography (SEC) fractions of the reconstituted alkylated dsMCs with the membrane associated entity and lipid after removal of detergent, FIG. 7 shows (b) tSEM image of SEC purified reconstituted transmembrane helix (Scale bar: 50 nm).

In a first aspect the present invention provides a minicircle-surrounded lipid bilayer, wherein the minicircle at least comprises nucleic acids or nucleic acid analogues.

The minicircle-surrounded lipid bilayer comprises at least one membrane associated entity. Preferably, the lipid bilayer is a disc-shaped lipid bilayer.

Embodiments of the invention encompass a minicircle at least comprising nucleic acids or nucleic acid analogues which are selected from ssDNA, dsDNA, RNA or oligonucleotide analogues (sometimes called Xeno DNA) such as PNA, LNA, spiegelmers, morpholino analogues, glycol nucleic acids, threose nucleic acids (TNA) and combinations thereof.

Embodiments of the invention encompass a minicircle further comprising peptides, polysaccharides, and bacterial aliphatic polyesters.

In further embodiments of the invention the minicircle is made of DNA surrounded lipid bilayer. In embodiments of the invention the DNA is selected from ssDNA or dsDNA.

According to the present invention ssDNA is interpreted as single-stranded DNA and dsDNA as double-stranded DNA.

Preferably, the minicircle surrounding the lipid-bilayer is made of DNA, wherein the DNA is dsDNA. By using dsDNA, a stable and more rigid circular shaped scaffold is provided enabling maximal control over size, shape and functionalization by use of DNA nanotechnology.

The DNA nanotechnology allows generation of arbitrarily shaped structures with A precision by a bottom-up self-assembly process. DNA structures can be functionalized with a large variety of artificial elements including small molecules, fluorophores, functional groups, biomolecules or inorganic nanoparticles in a modular and programmable fashion.

In embodiments of the invention the DNA surrounding the lipid bilayer comprises dsDNA, RNA or oligonucleotide analogues (sometimes called Xeno DNA) such as PNA, LNA, spiegelmers, morpholino analogues, glycol nucleic acids, threose nucleic acids and combinations thereof.

In embodiments of the invention the surrounding minicircle acts as a scaffold for the self-assembly of the lipid bilayer.

Further embodiments of the invention encompass that the minicircle comprises site-specific hydrophobic chemical entities, which are attached to the nucleic acids or nucleic acid analogues. Preferably the site-specific hydrophobic chemical entities are attached to the backbone of the nucleic acids or nucleic acid analogues, more preferably using phosphorothioate reactivity.

In further embodiments of the invention the site-specific hydrophobic chemical entities are selected from alkyl chains, such as methyl, ethyl, propyl, butyl or longer linear or branched aliphatic carbon chains. For example, the site-specific hydrophobic chemical entities are isobutyl-groups. In further embodiments the site-specific hydrophobic chemical entity is selected from linear or branched, saturated or unsaturated C1-C18 alkyl or aliphatic hydrocarbon chains, cholesterol groups, porphyrin groups, porphyrazin groups, a condensed aromatic system, a heteroaromatic molecule, block copolymers or combinations thereof.

In further embodiments of the invention, the attached site-specific hydrophobic chemical entities of the minicircle nucleic acids or nucleic acid analogues point inwards to the interior of the minicircle. After hybridization, a bilayer self-assembles after removal of the detergent in the interior of the modified nucleic acids or nucleic acid analogues of the minicircle upon addition of phospholipids.

In further embodiments of the invention, the attached site-specific hydrophobic chemical entities of circular dsDNA oligomers point inwards. When the hybridization reaction was followed by the addition of phospholipids, a bilayer self-assembled within the interior of the modified dsDNA minicircle.

As used herein, the term "membrane associated entity" refers to molecules, preferably peptides or proteins, which are associated to biological membranes, preferably molecules which interact with or are part of biological membranes. Embodiments of the invention encompass that the membrane associated entity is an integral membrane protein or a membrane-associated protein. The membrane associated entity can be selected from the group comprising G protein-coupled receptors (GPCRs), transmembrane receptors, pattern recognition receptors (PRRs), Toll-like receptors (TLRs), killer activated and killer inhibitor receptors (KARs and KIRs), complement receptors, Fc receptors, B cell receptors, T cell receptors, extracellular matrix-binding cell surface receptors, receptors from the integrin family, intercellular cell adhesion molecule, extra cellular matrix proteins, Cadherins, ion channels, ion pumps, carrier proteins or antigens.

In further embodiments of the invention the antigens are selected from the group of bacterial, viral, tumor-associated antigens or auto immunogenic antigens.

In further embodiments of the invention the minicircle-surrounded lipid bilayer further comprises a linker, wherein the linker is linear and wherein one end of the linker is attached to the minicircle-surrounded bilayer and the other end is a free end. Preferably, the linker is attached to the nucleic acids or nucleic acid analogues of the minicircle.

In further embodiments of the invention the linker is composed of ssDNA or dsDNA, RNA peptides, or oligonucleotide analogues (sometimes called Xeno DNA) such as PNA, LNA, spiegelmers, morpholino analogues, glycol nucleic acids, threose nucleic acids and combinations thereof.

In further embodiments of the invention the linker is used to address other molecules with complementary nucleic acids or nucleic acid analogues including dsDNA, RNA or oligonucleotide analogues (sometimes called Xeno DNA) such as PNA, LNA, spiegelmers, morpholino analogues, glycol nucleic acids, threose nucleic acids and combinations thereof, proteins, antibodies, or functionalized surfaces.

Further embodiments of the invention encompass that the linker is an oligonucleotide, capable of hybridizing to sequences of the nucleic acids or nucleic acid analogues that surround the lipid bilayer.

In further embodiments the linker is a ssDNA or RNA strand, which is attached to a surface or matrix so as to allow a site-specific attachment of the DNA surrounded lipid bilayer on the surface or matrix. Thus, a site-specific identification of interaction between the membrane associated entity and a target is achieved.

In further embodiments the linker comprises a binding entity. Preferably, the binding entity is at the free end of the linker. The binding entity is capable of binding a target or potential target that interacts with the membrane associated entity. Thereby, the linker forms a flexible loop that provides the target to the membrane associated entity. Thus, the interaction of the membrane associated entity and the target can be studied and kinetic data can be obtained in a specialized environment that minimizes possible errors due to the directed interaction.

In an embodiment of the invention, the membrane associated entity is a G protein-coupled receptor (GPCR) and the target is a ligand that binds to the G protein-coupled receptor or the membrane associated entity is an immune receptor and the target is an antigen that binds to the immune receptor or the membrane associated entity is an antigen and the target is an antigen binding entity, wherein the antigen binding entity is selected from the group of antibodies or antigen-binding fragments thereof, aptamers.

The antibody may be obtained from any species of animal, though preferably from a mammal such as human, simian, mouse, rat, rabbit, guinea pig, horse, cow, sheep, goat, pig, dog or cat. Preferably the antibodies are human or humanized antibodies. Nor is there a limitation on the particular class of antibody that may be used, including IgG1, IgG2, IgG3, IgG4, IgM, IgA1, IgA2, IgD and IgE antibodies. Antibody fragments include single-chain variable fragment (scFv), single chain antibodies, F(ab')2 fragments, Fab fragments, and fragments produced by a Fab expression library, with the only limitation being that the antibody fragments retain the ability to bind the antigen.

The antibodies may also be polyclonal, monoclonal, or chimeric antibodies, such as where an antigen binding region (e.g., F(ab')2 or hypervariable region) of a non-human antibody is transferred into the framework of a human antibody by recombinant DNA techniques to produce a substantially human molecule. Antigen-binding fragments, such as scFv, may be prepared therefrom. Antibodies to a selected antigen may be produced by immunization of various hosts including, but not limited to, goats, rabbits, rats, mice, humans, through injection with a particular protein or any portion, fragment or oligopeptide that retains immunogenic properties of the protein.

The antibodies or fragments thereof bind to antigens like CD2, CD3, CD4, CD8, CD10, CD19, CD20, CD22, CD23, CD33, CD38, CD44, CD52, CD99, CD123, CD274 and TIM-3, members of the epidermal growth factor receptor family (erb1, erb2, erb3, erb4 and mutants thereof), members of the ephrin receptor family (EphA1-10, EphB1-6), so called prostate specific antigens (e.g. prostate stem cell antigen PSCA, prostate specific membrane antigen PSMA), embryonic antigens (e.g. carcinoembryonic antigen CEA, fetal acethylcholine receptor), members of the vascular endothelia growth factor family (VEGFR 1-3), epithelia cell adhesion molecule EpCAM, alphafetoprotein AFP, members of the mucin protein family (e.g. MUC1, MUC16), follicle stimulating hormone receptor (FSHR), the human high molecular weight-melanoma-associated antigen (HMW-MAA), folate binding protein FBP, a-Folate receptor, ligands of the NKG2D receptor, members of the epithelia glycoprotein family (e.g. EGP-2, EGP-4), diasialoganglio-sides (e.g. GD2, GD3), members of the carbonic anhydrase family (e.g. CAIX), and members of the carbohydrate antigen family (e.g. Ley), including mutants of the named proteins and protein families. In addition, the antigens may be selected from cytoplasmic or nuclear antigens like the La/SSB antigen, members of the Rho family of GTPases, members of the high mobility group proteins and others. Likewise, the binding moiety of a target can be composed of the alpha and beta or the gamma and delta chains of a T cell receptor (TCR) or fragments thereof. Such TCR-derived binding moieties recognize and bind to peptides presented by human leukocyte antigen class (HLA) I and II protein complexes. Examples are, but are not limited to, TCRs specific for peptides derived from proteins like EGFR family, survivin, sry-like high motility group box (SOX) protein family, melanoma-associated antigens (e.g. autoimmunogenic cancer/testis antigen NY-ESO-1, members of the melanoma antigen family A MAGEA, the preferentially expressed antigen in melanoma PRAME), and leukemia-associated antigens (e.g. wilms tumor gene 1 WT1). The binding moiety of a target can also comprise ligands to proteins and protein complexes, further on referred as receptors. Such ligands may bind to, but are not limited to, cytokine receptors (e.g. IL-13 receptor), ligands of the NKG2D receptor, ligands to the EGFR family members, or auto-reactive TCRs.

In a further aspect the invention provides a method for preparation of minicircle-surrounded lipid bilayers. The method comprises the steps of:
a) providing a minicircle comprising at least double stranded nucleic acids or nucleic acid analogues,
b) mixing of the minicircle with lipids and the membrane associated entity in a detergent,
c) remove of the detergent,
d) self-assembly of the minicircle-surrounded lipid bilayer comprising the membrane associated entity.

Embodiments of the invention encompass a method for preparation of DNA-surrounded lipid bilayers. The method comprises the steps of:
a) providing a circular ssDNA strand,
b) providing a complementary ssDNA sequence or several partial complementary ssDNA sequences,
c) assembly of the subunits into dsDNA,
d) mixing of the dsDNA with lipids and the membrane associated entity in a detergent,
e) removal of the detergent, f) self-assembly of the DNA-surrounded lipid bilayer comprising the membrane associated entity.

Embodiments of the invention encompass the attachment of other functionalized molecules to the linker or the minicircle-surrounded lipid bilayer such as enzymes or quantum dots or chemically reactive groups that can be used for example in cycloadditions, thiolene reactions, Diels-Alder reaction, nucleophilic substitution, addition reactions to carbon-carbon double bonds, and general CLICK chemistry to form chemical bonds to other tags, labels or functionalized surfaces.

Embodiments of the invention encompass the removal of the detergent by dialysis.

In a further aspect the invention provides an assay comprising the minicircle-surrounded lipid bilayer according to the invention and a tag binding entity, wherein the tag binding entity binds to an immobilized tag.

In embodiments of the invention the tags are immobilized in the form of a microarray. By using the tags to direct the minicircle-surrounded lipid bilayer a site-directed assay is performed, which allows a direct mapping of the membrane associated entity of the lipid bilayer and the used target. Thus, a site-specific interaction of the membrane associated entity and the target is achieved.

Embodiments of the invention encompass that the tag is selected from a group consisting of aptamers, non-DNA-based natural or synthetic ligands of integral membrane proteins, protein tags, antibodies or fragments thereof.

Embodiments of the invention encompass minicircle-surrounded lipid bilayers according to the present invention, wherein the membrane associated entity is an antigen. The antigen presenting DNA surrounded lipid bilayer can be used for obtaining antibodies or antigen binding fragments thereof.

In a further aspect the invention provides a method for determining the interaction of a membrane associated entity and a target molecule. The method comprises the steps of
a) Providing an assay according to invention,
b) Providing a target molecule,
c) Determining the interaction of the at least one membrane associated entity and the target molecule by a method selected from the group of an optical detection method, quartz crystal microbalance (QCM) or by surface plasmon resonance (SPR). The optical detection method comprises FRET, fluorescence imaging and ELISA.

Embodiments of the invention encompass assays for interactions of ligands and test compounds with membrane proteins.

Embodiments of the invention encompass the targeting of membrane receptors by drugs aiming at modulating the binding affinity of the receptors to their cognate ligands, such as hormones, growth factors and others. To detect an influence of a compound on the receptor's ligand affinity, ligands can be covalently linked to the binding entity of the linker protruding from the rim of a minicircle-surrounded lipid bilayer, thereby allowing these ligands to reside permanently in the reaction volume of a receptor such that they equilibrate according to their natural "on" and "off" rates without diffusing away from the receptor even if the total concentration of the ligand is small. In the presence of a test compound that competes with the natural ligand-binding site or alters the ligand affinity by binding to the receptor at an allosteric site, the time spent by the minicircle-tethered ligand at the receptor is altered.

In an embodiment of the invention the binding entity of the linker is a 3' or 5' hydroxyl group of an oligonucleotide, preferably the protruding oligonucleotide. Preferably ligands with amino groups can be covalently linked to the 3' end of a protruding oligonucleotide.

Embodiments of the invention encompass the covalently linkage of dyes and chemical modifications with amino groups to the 3' or 5' hydroxyl group of an oligonucleotide, preferably the protruding oligonucleotide.

In a further embodiment of the invention the use of minicircle-surrounded lipid bilayers in an assay format is shown in the FIG. 1a, where the ligand is tethered to the minicircle surrounding lipid bilayer that contains the cognate membrane receptor. The sequence of the ssDNA tether is designed to carry the ssDNA (P) which is complementary to the protruding strand of the minicircle, a sufficiently long ssDNA linker sequence (L) that is not involved in hybridization to the minicircle, thereby ensuring space and flexibility for the movement of the ligand to reach its binding site on the receptor in the minicircle. L further contains a tag (T) that can hybridize with a "monitor oligonucleotide" (M).

The hybridization of M to T forms a locally stiffened and shortened double-helical base-paired M*T state. The shorter and straightened helical structure reduces the probability of the ligand to reach its receptor binding-site. The population of receptor-bound ligand states depends on the accessibility of T for M and is thus under the control of the dynamic equilibrium of T in either the exposed conformation when the ligand is not interacting with its receptor or in the spatially restricted conformation when free movement of the tether is prevented by the binding of the chemokine to its receptor. Therefore, binding of M populates the base-paired T*M state that prevents bending of the L sequence due to the shorter and stiffer dsDNA state, whereas ligand binding to the receptor stabilizes the bended form with a single-stranded L sequence, thereby diminishing accessibility of T for M. M can be covalently labeled with a fluorophore. The fluorescence conferred to the minicircle by binding of M, as observed for example in a single molecule experiment, will depend on the ability of an added drug to replace the chemokine directly or indirectly from its binding site. Therefore, it provides an optical signal that is a relative measure of the ability of a compound to attenuate the binding of a ligand to its membrane receptor.

Alternative optical readouts can be generated with the same scheme of T*M base pairing for example when M carries a quencher that abolishes fluorescence of a fluorophore coupled to the rim of the minicircle-surrounded lipid bilayer or the ligand. Likewise, M may carry a donor or acceptor for Förster resonance energy with another chromophore attached to the minicircle-surrounded lipid bilayer or one of its components.

Figure 1C:
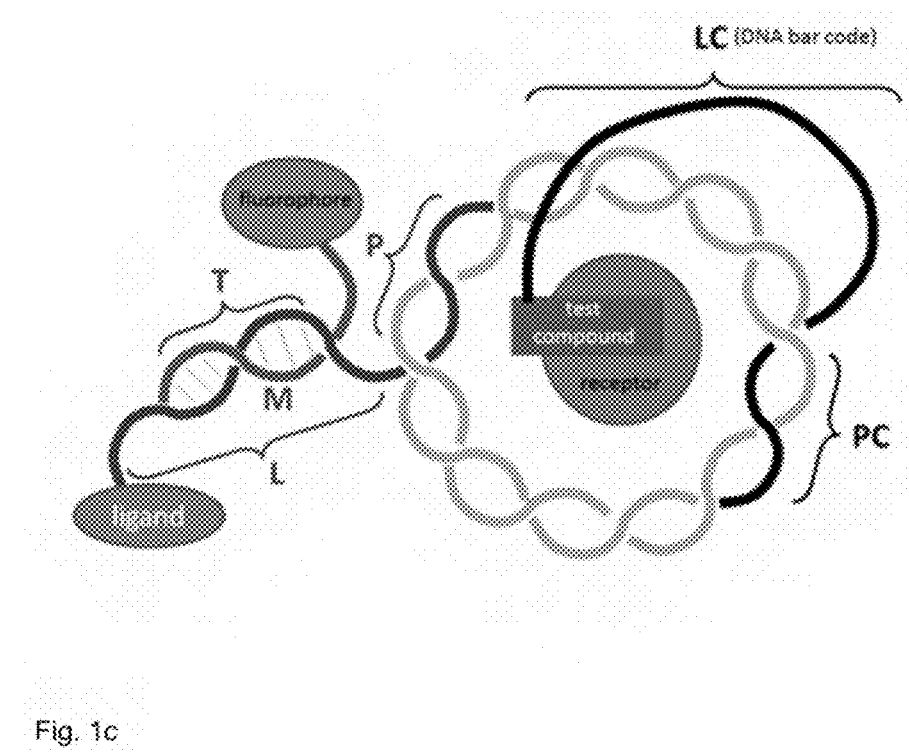

Further embodiments of the invention encompass that the assay can be designed for high throughput screening of test compounds when both a ligand and a receptor-targeting compound (test compound) are tethered to a minicircle (FIG. 1b). In this case a test compound library can be barcoded with a single-stranded oligonucleotide carrying a terminal sequence PC that is complementarity to a protruding strand of the minicircle followed by a sequence LC and a site for the covalent attachment of the test compound to the ssDNA (linker). Likewise, the ligand is covalently attached to a single-stranded oligonucleotide carrying a terminal sequence P that is complementary to a protruding strand of a minicircle followed by linker sequence L which terminates with the covalent attachment site for the ligand (FIG. 1c). L is designed such that it contains a target sequence T which is complementary to a monitoring oligonucleotide M. The competition of the compound and the ligand for the same binding site on the receptor in the minicircle-surrounded lipid bilayer leads to different populations of an exposed and a receptor-tethered state of L as described above: when the test compound binds stronger than the ligand sequence L will be exposed from the minicircle-surrounded lipid bilayer, whereas stronger ligand binding will bend L to the inside of the minicircle. The exposure of the T sequence is thus high when the test compound displaces the ligand from its receptor. In consequence M will bind. If MO is labeled with a fluorophore, the fluorescence of the minicircle-surrounded lipid bilayer can be detected for example in a single molecule assay in a confocal microscope or on a microarray format and the fluorescence properties of dyes locally attached to the minicircle or its components.

This format provides the additional advantage that the sequence LC can be designed as a "bar code" for the test compound that is covalently attached to that sequence. Using fluorescence-based sorting technologies allows separating minicircles with test compounds that have high receptor affinity. Amplification and sequencing of the separated oligonucleotides reveals the "bar code" of the test compounds that bind efficiently to the receptor. Thereby, this format can simultaneously screen many test compounds against a single receptor in its native membrane environment and can identify efficiently binding test compounds in the mixture. Using bar coding also in the receptor-containing minicircles, further extends the possibility of test compound screening to multiple receptors in a single assay.

Further embodiments of the invention encompass the use of the invention in medical applications. The assembly of membrane proteins in minicircle-surrounded lipid bilayers allows mimicking natural cell membrane surfaces by choosing corresponding lipid compositions and cell type-specific membrane proteins. Such surfaces play key roles in cell-cell communication as for example in the immune system or in blood clotting. The possibility of presenting membrane proteins in their natural lipid environment renders minicircle-surrounded lipid bilayers suitable for the specific interference with cell-cell contacts.

For example, integrins are surface receptors on immune cells that bind to a number of cell adhesion molecules such as intercellular adhesion molecule 1 (ICAM1) which itself is a glycosylated single transmembrane spanning membrane protein. The reconstitution of ICAM1 into minicircle-surrounded lipid bilayers opens the possibility to interfere with cell-cell communication for example between T-lymphocytes and the endothelium. The hybridization-mediated super-assembly of minicircle-surrounded lipid bilayers further enables generation of larger nano- to micron-sized arrays of membrane proteins that can be presented to a cell surface. The additional possibility to tether oligonucleotide-linked antibodies to the minicircles using hybridization to protruding ssDNA strands of the minicircles or the super-assembled structure allows targeting specific cells with antibody-linked minicircle-surrounded lipid bilayers. For example, ICAM1-reconstituted antibody labeled minicircle-surrounded lipid bilayers can be directed to T-cell-specific surface antigens, thereby attaching to the T-cell surface and presenting ICAM1 to bind to T-cell integrins as a stimulus that is typically provided by the cell contact with the endothelium.

Further embodiments of the invention encompass the use of minicircle-surrounded lipid bilayers for the production of antibodies against natively folded membrane proteins.

Mimicking specific cell surfaces by insertion of cell type-specific membrane proteins into minicircle-surrounded lipid bilayers in combination with cell type-specific lipids has potential for antibody production or vaccination. The production of antibodies against natively folded membrane proteins can be facilitated by eliciting an immune response by a membrane protein inside a minicircle-surrounded lipid bilayer rather than using non-folded fragments of the membrane protein for immunization of antigen-producing animals. Antibodies against the native folded state of a membrane protein are required for crystallization of membrane proteins and stabilization of conformational sub-states.

The antibody may be obtained from any species of animal, though preferably from a mammal such as human, simian, mouse, rat, rabbit, guinea pig, horse, cow, sheep, goat, pig, dog or cat. Preferably the antibodies are human or humanized antibodies. Nor is there a limitation on the particular class of antibody that may be used, including IgG1, IgG2, IgG3, IgG4, IgM, IgA1, IgA2, IgD and IgE antibodies. Antibody fragments include single-chain variable fragment (scFv), single chain antibodies, F(ab')2 fragments, Fab fragments, and fragments produced by a Fab expression library, with the only limitation being that the antibody fragments retain the ability to bind the antigen.

The antibodies may also be polyclonal, monoclonal, or chimeric antibodies, such as where an antigen binding region (e.g., F(ab')2 or hypervariable region) of a non-human antibody is transferred into the framework of a human antibody by recombinant DNA techniques to produce a substantially human molecule. Antigen-binding fragments, such as scFv, may be prepared therefrom. Antibodies to a selected antigen may be produced by immunization of various hosts including, but not limited to, goats, rabbits, rats, mice, humans, through injection with a particular protein or any portion, fragment or oligopeptide that retains immunogenic properties of the protein. The antibodies or fragments thereof that bind to antigens like CD2, CD3, CD4, CD8, CD10, CD19, CD20, CD22, CD23, CD33, CD38, CD44, CD52, CD99, CD123, CD274 and TIM-3, members of the epidermal growth factor receptor family (erb1, erb2, erb3, erb4 and mutants thereof), members of the ephrin receptor family (EphA1-10, EphB1-6), so called prostate specific antigens (e.g. prostate stem cell antigen PSCA, prostate specific membrane antigen PSMA), embryonic antigens (e.g. carcinoembryonic antigen CEA, fetal acethylcholine receptor), members of the vascular endothelia growth factor family (VEGFR 1-3), epithelia cell adhesion molecule EpCAM, alphafetoprotein AFP, members of the mucin protein family (e.g. MUC1, MUC16), follicle stimulating hormone receptor (FSHR), the human high molecular weight-melanoma-associated antigen (HMW-MAA), folate binding protein FBP, a-Folate receptor, ligands of the NKG2D receptor, members of the epithelia glycoprotein family (e.g. EGP-2, EGP-4), diasialogangliosides (e.g. GD2, GD3), members of the carbonic anhydrase family (e.g. CAIX), and members of the carbohydrate antigen family (e.g. Ley), including mutants of the named proteins and protein families. In addition, the antigens may be selected from cytoplasmic or nuclear antigens like the La/SSB antigen, members of the Rho family of GTPases, members of the high mobility group proteins and others. Likewise, the binding moiety of a target can be composed of the alpha and beta or the gamma and delta chains of a T cell receptor (TCR) or fragments thereof. Such TCR-derived binding moieties recognize and bind to peptides presented by human leukocyte antigen class (HLA) I and II protein complexes. Examples are, but are not limited to, TCRs specific for peptides derived from proteins like EGFR family, survivin, sry-like high motility group box (SOX) protein family, melanoma-associated antigens (e.g. autoimmunogenic cancer/testis antigen NY-ESO-1, members of the melanoma antigen family A MAGEA, the preferentially expressed antigen in melanoma PRAME), and leukemia-associated antigens (e.g. wilms tumor gene 1 WT1). The binding moiety of a target can also comprise ligands to proteins and protein complexes, further on referred as receptors. Such ligands may bind to, but are not limited to, cytokine receptors (e.g. IL-13 receptor), ligands of the NKG2D receptor, ligands to the EGFR family members, or auto-reactive TCRs.

Further embodiments of the invention encompass the use of the DNA-encircled lipid bilayers (DEBs) for targeting cells for T-cell interactions.

Minicircle-surrounded lipid bilayers can be used to reconstitute CD1 molecules which are membrane proteins that present lipids to natural killer T-cells (FIG. 2). This elicits an immune response by the T-cell leading to killing of the lipid-presenting target CD1 cell. CD1-loaded minicircle-surrounded lipid bilayers can be produced according to the general methods.

The invention exploits the high potential of chemical specificity and structural control provided by DNA nano-technology to generate size-controlled and nearly monodisperse discoidal lipid bilayers without the need of MSPs or other polymers. To this end, mini plasmids are produced according to known procedures and chemically modified with hydrophobic groups such that they self-assemble lipid bilayers in their interior. Lipid association and reconstitution with membrane proteins can be accomplished in very similar manner as used for the systems described in Prior art.

The invention differs from existing procedures by its independence of structure-stabilizing proteins and statistical mixtures of polymers, whereby the main sources for structural heterogeneity and restrictions in further implementation of chemical specificity are avoided. The procedure is thus independent of recombinant protein expression and mutagenesis (MSPs) and allows size variation far beyond the sizes accessible with MSPs.

In contrast to existing methods, the invention uses mini-circles comprising nucleic acids or nucleic acid analogues for which established methods allow simple chemical modifications and predictable assembly into ring-shaped double stranded DNA (dsDNA) of variable size which can then be filled with various lipid mixtures. Lipid association and membrane protein insertion can be performed in accordance with existing methods.

According to the invention, the self-assembly of the nucleic acid minicircles with lipids is enabled by the site-specific attachment of hydrophobic chemical entities, for example alkyl chains, to the nucleic acid back bone at predictable positions, such that these hydrophobic modifications point inside the ring structure. The admixture of positively charged lipids can further be used to enforce the interaction of the lipid with the negatively charged nucleic acid backbone by an electrostatic contribution. The largely free choice of nucleic acid sequences allows adjusting the thermal melting temperature of the final assembly. Furthermore, protruding single stranded DNA (ssDNA) strands can be introduced as attachment sites for other nanoscale mini-circle-surrounded lipid bilayers or complementary strands immobilized on a substrate surface.

In comparison to the state of the art, the invention enables the production of nano-scaled lipid bilayers of precise size orthogonal coupling to other chemical entities using nucleic acids complementarity for supramolecular assembly and surface attachment. Importantly, nucleic acids complementarity can also be used for the geometrical design of other components within the minicircle-surrounded lipid bilayers such as the membrane protein, a ligand or a drug by their attachment to the rim of the minicircle-surrounded lipid bilayers, provided the membrane protein, ligand or drug carries a ssDNA segment that is complementary to a ssDNA strand protruding from the rim of the minicircle-surrounded lipid bilayers. An important advantage over non-programmable assemblies is the DNA hybridization-mediated linkage of binding partners for a membrane protein to the minicircle rim, because the binding partners have a constant high local concentration near the protein without being able to diffuse out of the reaction volume. Thereby, the total concentration of binding partners in an assay solution can be vanishingly small. In summary, the invention provides a technology platform with high structural control of nucleic acid, lipid, protein, ligand assemblies and superstructures thereof which is entirely independent of MSPs. Such a platform opens new applications in pharmacology and x-ray diffraction-based Structural Biology of membrane proteins ranging from single particle to designed crystals of membrane proteins.

The improvements generated by the invention over existing methods for the production of nano-scaled lipid bilayers originate in the much larger freedom in structural design and programmability of nucleic acid nanostructures as compared to polymers and MSPs.

For the purpose of realizing the invention, it is also beneficial to combine the variants and embodiments according the invention described previously and the features of the claims in any order.

EXAMPLES

The following examples will illustrate the practice of the present invention in its preferred embodiments. Other embodiments with the scope of the claims herein will be apparent to one skilled in the art from consideration of the specification and practice of the invention as disclosed herein. It is intended, that the specification together with the example be considered exemplary only with the scope and spirit of the invention being indicated by the claims which follow.

Example 1

A double-stranded minicircle (dsMC) composed of a circularized 147 nt long oligonucleotide, e.g. DNA and seven identical short oligonucleotides (21 nt) was designed. With a rise of 0.335 nm/bp, the outer diameter is expected to be 16.7 nm and the inner diameter 14.7 nm.

To enable interactions of the negatively charged hydrophilic DNA and the lipids, several oligonucleotides modifications have been previously employed including cholesterol modifications, porphyrins or phospholipids. To make the approach as modular, scalable and cost-effective as possible, and to be able to introduce it without long linkers even in middle of an oligonucleotide, phosphorothioates were alkylated with alkane iodides (FIG. 3a). For this, commercially available oligonucleotides containing two or four internal phosphorothioates were reacted with a large excess of ethyl iodide, butyl iodide or decyl iodide. The product was HPLC purified and the successful alkylation confirmed by ESI mass spectrometry.

To control the inside and outside of the toroidal dsDNA, the sequence contained 14 A-tracts. A-tracts are intrinsically curved DNA motifs consisting of five or six consecutive A-T base pairs in which the minor groove is compressed (FIG. 3d) and thus dictate the curvature of the dsMC.

To assemble the alkyl-modified dsMC, a ssMC was synthesized from one long oligonucleotide (147 nt) by splint ligation (FIG. 3b). For this, the ends of that oligonucleotide were annealed to a splint oligonucleotide and enzymatically phosphorylated and ligated. Residual linear long oligonucleotides, splints and linear side products were enzymatically removed by a treatment with Exonuclease I/III (FIG. 3 b-c). Next, the ssMC were hybridized with an excess of the alkylated oligonucleotides by slow cooling. The excess of oligonucleotides was removed by ultrafiltration and the complex was analyzed by native agarose gel electrophoresis (FIG. 3e), atomic force microscopy and transmission scanning electron microscopy.

Finally, the alkylated dsMCs were filled with a lipid bilayer (FIG. 3 f-g). Similar to nanodisc formation with MSPs, removal of detergent from a detergent-solubilized mix of the alkylated dsDNA mini circles and stoichiometric amounts of phospholipids leads to the self-assembly of the components into nano-scaled discoidal particles.

AFM imaging of the dsMCs (R=4 butyl) and DEBs revealed a doubling of the height due to the addition of the lipid bilayer (FIG. 4 a-c). The tSEM images (FIG. 4 d, f) also confirm the presence of a lipid bilayer in the DEBs. Short (14 ethyl) and longer alkyl chains (28 decyl), produced DEBs (FIG. 4 e,f), but DEBs with longer alkyl chains formed with higher yields (FIG. 5a-c).

DEBs were purified either by size exclusion chromatography or ultracentrifugation (FIG. 5a-b), where DEBs formed one sharp band which contained both lipids and DNA.

The association of a membrane associated entity with DEBs can be achieved by preparing detergent-solubilized mixtures of lipids, alkylated dsMCs and membrane associated entities from which the detergent is removed. For detergent removal, a cholate-solubilized mix of lipids and alkylated (28 decyl chains) dsMCs with poly-alanine peptides was dialyzed. Depending on the adjusted ratio (lipid:peptide:alkyl-dsMC, 300:10:1), the resulting material will contain various amounts of aggregates of lipids and free dsMCs in addition to the desired peptide-associated DEBs. Due to the restricted size range of DEBs as compared to the variable sizes of non-specific aggregates, the peptide-associated DEBs can be preferentially obtained from the mixture by size exclusion chromatography (SEC).

FIG. 6 shows vibrational spectra obtained from consecutively collected 1 mL SEC fractions of the reconstituted alkylated dsMCs with the poly-alanine peptide and di-myristoyl-phosphatidylcholine (DMPC) after removal of 30 mM sodium cholate. Fraction 3 eluted in the size range expected for DEBs and contained the three components as revealed by infrared spectroscopy (DMPC absorption at 1015 cm$^{-1}$, peptide between 1500 and 1700 cm$^{-1}$, DNA at 1238 cm$^{-1}$). In contrast, fractions one and four were dominated by DMPC, whereas fraction two was dominated by DNA and poly-alanine peptide with little contribution from DMPC.

Example 2

The reconstitution of a transmembrane helix into DEBs can be achieved by preparing detergent-solubilized mixtures of lipids, alkylated dsMCs and transmembrane helices from which the detergent is removed. For example, a n-Dodecyl β-D-maltoside-solubilized mix of lipids and alkylated (28 decyl chains) dsMCs with transmembrane helices of rhodopsin was dialyzed for detergent removal. Depending on the adjusted ratio (lipid:helix:alkyl-dsMC, 350:5:1), the resulting material will contain various amounts of aggregates of lipids and free dsMCs in addition to the desired the DEBs with reconstituted helices. Due to the restricted size range of DEBs as compared to the variable sizes of non-specific aggregates, the DEBs with reconstituted helices can be preferentially purified from the mixture by size exclusion chromatography (SEC). The purified product was imaged by tSEM showing the reconstituted transmembrane helix (marked by black arrows).

Example 3

A double-stranded minicircle (dsMC) composed of a circularized 147 nt long DNA and seven identical short oligonucleotides (21 nt) was designed. With a rise of 0.335 nm/bp, the outer diameter is expected to be 16.7 nm and the inner diameter 14.7 nm.

To enable interactions of the negatively charged hydrophilic DNA and the lipids, several oligonucleotides modifications have been previously employed including cholesterol modifications, porphyrins or phospholipids. Furthermore, phosphorothioates were alkylated with alkane iodides. For this, commercially available oligonucleotides containing two or four internal phosphorothioates were reacted with a large excess of ethyl iodide, butyl iodide or decyl iodide. The product was HPLC purified and the successful alkylation confirmed by ESI mass spectrometry.

To control the inside and outside of the toroidal dsDNA, the sequence contained 14 A-tracts. A-tracts are intrinsically curved DNA motifs consisting of five or six consecutive A-T base pairs in which the minor groove is compressed and thus dictate the curvature of the dsMC.

To assemble the alkyl-modified dsMC, a ssMC was synthesized from one long oligonucleotide (147 nt) by splint ligation. For this, the ends of that oligonucleotide were annealed to a splint oligonucleotide and enzymatically phosphorylated and ligated. Residual linear long oligonucleotides, splints and linear side products were enzymatically removed by a treatment with Exonuclease I/III. Next, the ssMC were hybridized with an excess of the alkylated oligonucleotides and an excess of a 20 nt ssDNA complementary to a 10 nt sequence of the DNA minicircle as linker by slow cooling. The linker is modified by a biotin molecule (tag binding entity) by CLICK chemistry.

The excess of oligonucleotides was removed by ultrafiltration and the complex was analyzed by native agarose gel electrophoresis, atomic force microscopy and transmission scanning electron microscopy.

The alkylated dsMCs were filled with a lipid bilayer. The removal of detergent from a detergent-solubilized mix of the alkylated dsDNA mini-circles and stoichiometric amounts of phospholipids leads to the self-assembly of the components into nano-scaled discoidal particles.

DEBs were purified either by size exclusion chromatography or ultracentrifugation, where DEBs formed one sharp band which contained both lipids and DNA.

The association of a membrane associated entity with DEBs is achieved by preparing a cholate-solubilized (30 mM sodium cholate) mixture of lipids (di-myristoyl-phosphatidylcholine (DMPC), alkylated (28 decyl chains) dsMCs and poly-alanine peptides from which the detergent is removed by dialysis. The peptide-associated DEBs can be preferentially obtained from the mixture by size exclusion chromatography (SEC).

The biotin-modified minicircle-surrounded lipid bilayer comprising poly-alanine peptides can interact with a Strep-Tag immobilized in microtiter plates.

CITED NON-PATENT REFERENCES

1. N. C. Seeman, H. F. Sleiman, DNA nanotechnology. *Nat. Rev.* Mater. 3, natrevmats201768 (2017).
2. T. L. Schmidt et al., Polyamide Struts for DNA Architectures. *Angew Chem Int Ed.* 46, 4382-4384 (2007).
3. T. L. Schmidt, A. Heckel, Construction of a Structurally Defined Double-Stranded DNA Catenane. *Nano Lett.* 11, 1739-1742 (2011).
4. M. Langecker, V. Arnaut, J. List, F. C. Simmel, DNA Nanostructures Interacting with Lipid Bilayer Membranes. *Acc. Chem. Res.* 47, 1807-1815 (2014).
5. S. D. Perrault, W. M. Shih, Virus-Inspired Membrane Encapsulation of DNA Nanostructures To Achieve In Vivo Stability. *ACS Nano.* 8, 5132-5140 (2014).
6. Z. Zhang, Y. Yang, F. Pincet, M. C. Llaguno, C. Lin, Placing and shaping liposomes with reconfigurable DNA nanocages. *Nat. Chem.* 9, 653-659 (2017).

The invention claimed is:

1. A minicircle-surrounded lipid bilayer at least comprising one membrane associated entity, wherein the minicircle comprises at least nucleic acids or nucleic acid analogues, and wherein the membrane associated entity is selected from peptides and proteins which are associated to biological membranes.

2. The minicircle-surrounded lipid bilayer according to claim 1, wherein the nucleic acids or nucleic acid analogues are selected from ssDNA, dsDNA, RNA or oligonucleotide analogues such as PNA, LNA, spiegelmers, morpholino analogues, glycol nucleic acids, threose nucleic acids and combinations thereof.

3. The minicircle-surrounded lipid bilayer according to claim 1, wherein the minicircle comprises site-specific hydrophobic chemical entities, which are attached to the nucleic acid backbone.

4. The minicircle-surrounded lipid bilayer according to claim 1, wherein the attached site-specific hydrophobic chemical entities of the minicircle nucleic acids or nucleic acid analogues point inwards to the interior of the minicircle.

5. The minicircle-surrounded lipid bilayer according to claim 3, wherein the site-specific hydrophobic chemical entities are selected from the group consisting of linear or branched, saturated or unsaturated C1-C18 alkyl or aliphatic hydrocarbon chains, cholesterol groups, porphyrin groups, porphyrazin groups, a condensed aromatic system, a heteroaromatic molecule or combinations thereof.

6. The minicircle-surrounded lipid bilayer according to claim 1, wherein the membrane associated entity is an integral membrane protein or a membrane-associated protein.

7. The minicircle-surrounded lipid bilayer according to claim 1, wherein the minicircle comprises a linker, wherein the linker is linear and wherein one end of the linker is attached to the minicircle and the other end is a free end.

8. The minicircle-surrounded lipid bilayer according to claim 7, wherein the linker is an oligonucleotide, capable of hybridizing to sequences of the nucleic acids or nucleic acid analogues that surround the lipid bilayer.

9. The minicircle-surrounded lipid bilayer according to claim 8, wherein the linker comprises a binding entity.

10. A method for preparation of minicircle-surrounded lipid bilayers comprising the steps of:

a) providing a minicircle comprising at least double stranded nucleic acids or nucleic acid analogues,
b) mixing of the minicircle with lipids and a membrane associated entity in a detergent, wherein the membrane associated entity is selected from peptides and proteins which are associated to biological membranes,
c) removing the detergent, and
d) self-assembly of the minicircle-surrounded lipid bilayer comprising the membrane associated entity.

11. The minicircle-surrounded lipid bilayer according to claim 1 and a tag binding entity, wherein the tag binding entity binds to an immobilized tag.

12. The minicircle-surrounded lipid bilayer according to claim 1 and a tag binding entity, wherein the tag binding entity binds to an immobilized tag, and wherein tags are immobilized in the form of a microarray.

13. The minicircle-surrounded lipid bilayer according to claim 1 and a tag binding entity, wherein the tag binding entity binds to an immobilized tag, wherein the tag is selected from the group consisting of aptamers, non-DNA-based natural or synthetic ligands of integral membrane proteins, protein tags, antibodies or fragments thereof.

14. A method for determining the interaction of a membrane associated entity and a target molecule comprising the steps:

a) providing the minicircle-surrounded lipid bilayer according to claim 1 and a tag binding entity, wherein the tag binding entity binds to an immobilized tag,
b) providing a target molecule, wherein the minicircle-surrounded lipid bilayer is directed to the target molecule, and
c) determining the interaction of the at least one membrane associated entity and the target molecule by a method selected from the group of an optical detection method, quartz crystal microbalance or by surface plasmon resonance (SPR).

15. The minicircle-surrounded lipid bilayer according to claim 2, wherein the minicircle comprises site-specific hydrophobic chemical entities, which are attached to the nucleic acid backbone.

16. The minicircle-surrounded lipid bilayer according to claim 15, wherein the attached site-specific hydrophobic chemical entities of the minicircle nucleic acids or nucleic acid analogues point inwards to the interior of the minicircle.

17. The minicircle-surrounded lipid bilayer according to claim 16, wherein the site-specific hydrophobic chemical entities are selected from the group consisting of linear or branched, saturated or unsaturated C1-C18 alkyl or aliphatic hydrocarbon chains, cholesterol groups, porphyrin groups, porphyrazin groups, a condensed aromatic system, a heteroaromatic molecule or combinations thereof.

18. The minicircle-surrounded lipid bilayer according to claim 17, wherein the membrane associated entity is an integral membrane protein or a membrane-associated protein.

19. The minicircle-surrounded lipid bilayer according to claim 18, wherein the minicircle comprises a linker, wherein the linker is linear and wherein one end of the linker is attached to the minicircle and the other end is a free end.

20. The minicircle-surrounded lipid bilayer according to claim 19, wherein the linker is an oligonucleotide, capable of hybridizing to sequences of the nucleic acids or nucleic acid analogues that surround the lipid bilayer.

* * * * *